United States Patent [19]

Hendricks

[11] 3,965,147

[45] June 22, 1976

[54] PHOSPHONOCARBOXYLIC ACID ESTERS

[75] Inventor: Udo-Winfried Hendricks, Cologne, Germany

[73] Assignee: Bayer Aktiengesellschaft, Leverkusen-Bayerwerk, Germany

[22] Filed: May 6, 1974

[21] Appl. No.: 467,149

[30] Foreign Application Priority Data
May 5, 1973 Germany.............................. 2322705

[52] U.S. Cl.................................. 260/478; 8/18 R; 8/90; 8/179; 260/485 J
[51] Int. Cl.$^2$.......................................... C07F 9/38
[58] Field of Search.......................... 260/478, 485 J

[56] References Cited
UNITED STATES PATENTS

| | | | |
|---|---|---|---|
| 3,125,555 | 3/1964 | Paré et al............................ | 260/478 |
| 3,192,205 | 6/1965 | Depoorter et al. ................. | 260/478 |
| 3,755,411 | 8/1973 | Henrick et al...................... | 260/478 |

OTHER PUBLICATIONS

Wagner et al., Synthetic Organic Chem., (1953).

*Primary Examiner*—James A. Patten
*Attorney, Agent, or Firm*—Plumley and Tyner

[57] ABSTRACT

Phosphonocarboxylic acid esters of the formula

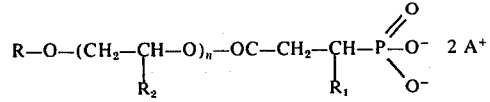

in which R, $R_1$, $R_2$, n and A have the meaning, given in the disclosure, and a process for their manufacture. The new compounds can be used as auxiliaries in dyeing and printing textile materials containing polyester fibres.

6 Claims, No Drawings

PHOSPHONOCARBOXYLIC ACID ESTERS

The invention relates to phosphonocarboxylic acid esters of the formula

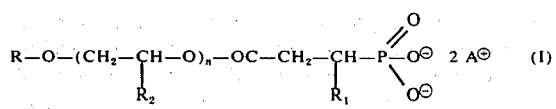   (I)

in which

R represents a $C_8$–$C_{22}$-alkyl radical, preferably a $C_{16}$–$C_{22}$-alkyl radical, a $C_8$–$C_{22}$-alkenyl radical, preferably a $C_{16}$–$C_{22}$-alkenyl radical, or a $C_8$–$C_{12}$-alkylphenyl radical, $R_1$ represents hydrogen or the

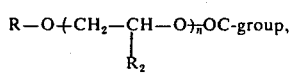-group, $R_2$ represents the methyl group or preferably hydrogen, $n$ represents a number from 1 to 10, preferably from 1 to 4, and A represents hydrogen, an alkali metal ion or, preferably, an ammonium ion, a process for their preparation, and their use as auxiliaries in dyeing and printing textile materials containing polyester fibres.

The following may be mentioned as examples of R:

As $C_8$–$C_{22}$-alkyl radicals, the n-octyl, n-decyl, n-dodecyl, tetradecyl, palmityl, stearyl and behenyl radicals; as $C_8$–$C_{22}$-alkenyl radicals, the decenyl, tetradecenyl and oleyl radicals; as $C_8$–$C_{12}$-alkyl-phenyl radicals, the i-octyphenyl, i-nonyl-phenyl and dodecyl-phenyl radical.

Possible alkali metal ions are preferably the sodium ion and potassium ion and possible ammonium ions are the ammonium ion and alkylammonium ions, such as the triethylammonium ion, the cyclohexylammonium ion and the mono-, di- or tri-$C_2$–$C_4$-hydroxyalkylammonium ions, for example the monoethanolammonium ion, the diethanolammonium ion and the tripropanolammonium ion.

The compounds of the formula I are prepared by esterifying alkoxylated alcohols and alkylphenols of the formula II

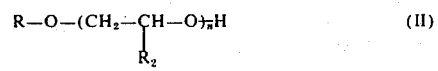   (II)

in which

R, $R_2$ and $n$ have the meaning indicated under the formula I with phosphonocarboxylic acids of the formula III

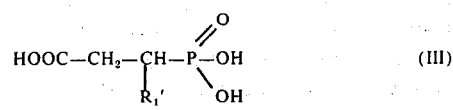   (III)

in which $R_1'$ represents a hydrogen atom or the carboxyl group at temperatures of 80°–200°C, preferably 120°–160°C, employing at least 1 mol of the compound II per carboxyl group in the phosphonocarboxylic acids of the formula III, and optionally subsequently neutralising the phosphonocarboxylic acid esters produced. The esterification can optionally be carried out in solvents or diluents which are inert under the reaction conditions, for example in toluene, xylene, chlorobenzene or dichloroethane. The water produced in the esterification reaction is removed continuously from the reaction mixture, for example by passing in a stream of air, applying a vacuum, distillation or azeotropic distillation with a suitable solvent, for example toluene.

Some representatives of the phosphonocarboxylic acid esters according to the invention, of the formula I, are listed in the table which follows:

Table

| R | $R_1$ | $R_2$ | n | A |
|---|---|---|---|---|
| $C_{12}H_{25}$—⟨phenyl⟩– | H | H | 10 | Na |
| $C_{18}H_{37}$— | H | H | 4 | $H_3N$—$C_2H_4$—OH |
| Oleyl | H | H | 2 | $H_2N(C_2H_4OH)_2$ |
| $CH_3(CH_2)_3$—CH($C_2H_5$)—$CH_2$— | $CH_3$–($CH_2$)$_3$–CH($C_2H_5$)–$CH_2$–O–($CH_2$–$CH_2$–O)$_2$OC | H | 2 | Na |
| $C_9H_{19}$—⟨phenyl⟩– | $C_9H_{19}$—⟨phenyl⟩–O–($CH_2$—$CH_2$—O)$_2$OC— | H | 2 | $H_2N(C_2H_4OH)_2$ |
| $C_9H_{19}$—⟨phenyl⟩– | $C_9H_{19}$—⟨phenyl⟩–O–($CH_2$—$CH_2$—O)$_4$OC— | H | 4 | $H_2N(C_2H_4OH)_2$ |
| $C_{12}H_{25}$— | $C_{12}H_{25}$—O—($CH_2$—$CH_2$—O)$_2$OC— | H | 2 | $NH_4$ |
| $C_{18}H_{37}$— | $C_{18}H_{37}$—O—($CH_2$—$CH_2$—O)$_6$OC— | H | 6 | Na |
| Oleyl- | Oleyl-O—($CH_2CH_2O$)$_2$—OC | H | 2 | $H_2N(C_2H_4OH)_2$ |
| $C_{12}H_{25}$— | H | $CH_3$ | 2 | $H_3N$—$C_2H_4$—OH |
| $C_8H_{17}$—⟨phenyl⟩– | H | H | 4 | Na |

The phosphonocarboxylic acid esters according to the invention, of the formula I, are valuable auxiliaries for dyeing textile materials containing polyester fibres. In particular, the addition of the compounds to the customary dyebaths when dyeing woven or knitted piece goods of polyester fibres or of their mixtures with natural fibres, such as wool and cotton, or synthetic fibres, such as polyamides, for example polyhexamethylenediamine adipate, poly-ε-caprolactam or poly-ω-aminoundecanoic acid, prevents the formation of running creases in the woven fabrics or knitted fabrics and at the same time substantially improves the handle of the textile materials.

In these properties, namely the prevention of creasing and the improvement of handle, the compounds according to the invention are superior to the phosphonic acid esters described in U.S. Pat. No. 3,300,337. As compared to the phosphonic acid esters described in German Offenlegungsschrift (German Published Specification) No. 1,668,073, the phosphonocarboxylic acid esters according to the invention display the advantage of being substantially simpler to prepare. The phosphonocarboxylic acid esters according to the invention provide dyeing technology, for a special purpose in which the known auxiliaries do not suffice, with new effective auxiliaries which in addition have the advantage that they can be prepared in a simple manner from readily accessible starting materials.

As examples of polyester fibres there may be mentioned those of polyethylene glycol terephthalate, poly-1,4-bis-(hydroxymethyl)-cyclohexane terephthalate and poly-p-hydroxyethoxy-benzoate.

The polyester fibres are dyed in the known manner, that is to say with disperse dyestuffs in the presence of carriers at 90°–110°C, or under HT conditions (120° – 130°C). In addition to the dyestuffs, carriers and compounds of the formula I, the dyebaths can contain the auxiliaries customary for these dyeing processes, for example dispersing agents of the type of dinaphthylmethane-disulphonate, agents which increase the migrating capacity of the disperse dyestuffs, such as o-hydroxydiphenyl, and agents which improve the evenness of the dyeing, such as ethoxylated alcohols or carboxylic acids.

The amounts in which the compounds according to the invention, of the formula I, are added to the dyebaths, can vary within wide limits; in general, additions of 1–3 g per litre of dyeing liquor have proved successful.

The dyeing of the polyester materials in the presence of the phosphonocarboxylic acid esters according to the invention is carried out, for example, by introducing the goods to be dyed into the liquor which has been warmed to about 50° – 60°C, and which contains the disperse dyestuff, the requisite dyeing auxiliaries and a compound of the formula I, added salts, such as sodium acetate, and also acids, such as acetic acid or sulphuric acid, subsequently raising the temperature of the dyebath to 120° – 130°C over the course of 30 – 45 minutes and then keeping the dyebath at this temperature until it is exhausted.

In addition, the phosphonocarboxylic acid esters of the formula I, according to the invention, produce a substantial acceleration of the fixing of the dyestuff when dyeing and printing textile materials of polyester or cellulose triacetate with disperse dyestuffs. The addition of 5 to 50 g. preferably 10 to 30, per litre of padding liquor or per kg of printing paste results in the same, or often even better, dyestuff yield at fixing temperatures below 200°C, for example at temperatures of 160° to 180°C, as, or than, with customary fixing at 200° to 210°C.

The parts indicated in the examples which follow are parts by weight unless stated otherwise.

EXAMPLE 1

40 parts of phosphonosuccinic acid and 143 parts of a technical octadecenol which has been ethoxylated with two ethylene oxide molecules are mixed with 300 parts of xylene. The resulting water (8.5 parts) is distilled off azeotropically whilst heating to 130°– 150°C. After completion of the reaction, the xylene is distilled off in vacuo. 171 parts of the compound of the formula

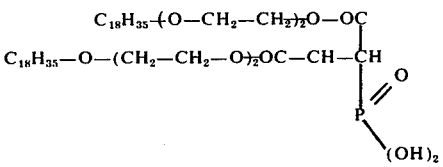

are left as a brownish, highly viscous oil.

Acid number: calculated: 128, found: 125.
Phosphorus content: calculated: 3.54%, found: 3.4%.

The free acid is converted into its mono-diethanolamine salt by addition of 50 parts of water and 21 parts of diethanolamine. This salt dissolves in hot water to give an emulsion.

EXAMPLE 2

54 parts of phosphonopropionic acid and 125 parts of a technical octadecenol which has been ethoxylated with two molecules of ethylene oxide are mixed and heated to 130°– 135°C in a waterpump vacuum until no further water distills off. 166 parts of the compound of the formula

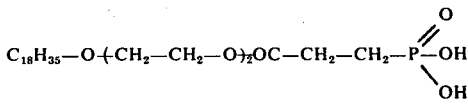

are obtained as a highly viscous, brownish syrup.

Acid number: calculated: 228, found: 221.
Phosphorus content: calculated: 6.29%, found: 6.0%.

The free acid is converted into its mono-diethanolamine salt by mixing with 60 parts of isopropanol, 300 parts of water and 37 parts of diethanolamine.

EXAMPLE 3

40 parts of phosphonosuccinic acid and 123 parts of a nonylphenol which has been ethoxylated with two molecules of ethylene oxide are mixed with 400 parts of xylene. The resulting water of reaction (8.2 parts) is distilled off azeotropically by heating to 150°– 160°C. After completion of the esterification, the xylene is distilled off in vacuo. 156 parts of the compound of the formula

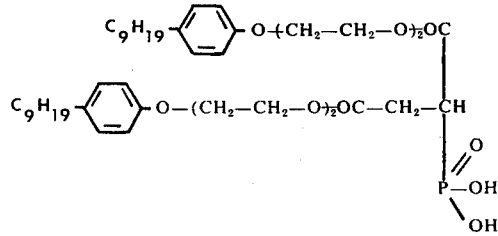

remain as a pale brownish-coloured highly viscous syrup.

Acid number: calculated: 144, found: 147.
Phosphorus content: calculated: 3.98%, found: 3.7%.

The free acid is converted into its diethanolamine salt by addition of 24 parts of ethanolamine at 60° - 70°C. This salt is obtained in the form of a clear, viscous, brown oil.

EXAMPLE 4

99 parts of phosphonosuccinic acid and 397 parts of a nonylphenol which has been ethoxylated with four molecules of ethylene oxide are mixed with 700 parts of toluene. The water of reaction (18 parts) is distilled off azeotropically by heating to 120° – 130°C. After completion of the reaction, the toluene is distilled off in vacuo. 475 parts of the compound of the formula

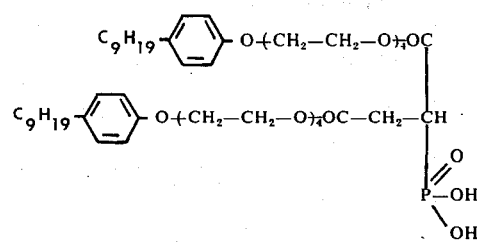

remain as a clear, yellowish, highly viscous oil.
Acid number: calculated: 117, found: 105.
Phosphorus content: calculated: 3.25% found: 3.0%.

The free salt is converted into its di-triethanolamine salt by dissolving in 400 parts of water and 149 parts of triethanolamine.

EXAMPLE 5

99 parts of phosphonosuccinic acid and 660 parts of a nonylphenol which has been ethoxylated with ten molecules of ethylene oxide are mixed with 600 parts of toluene. The resulting water is distilled off by heating to 120° – 130°C. After completion of the reaction, the toluene is distilled off in vacuo. 736 parts of the compound of the formula

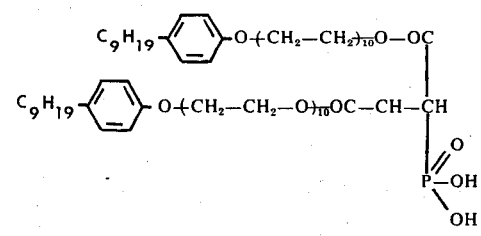

are obtained as a pale brownish-coloured viscous oil.
Acid number: calculated: 76, found: 80.
Phosphorus content: calculated: 2.09%, found: 1.9%.

The free acid is converted into its di-triethanolamine salt by addition of 149 parts of triethanolamine.

EXAMPLE 6

58 parts of phosphonopropionic acid and 252 parts of a nonylphenol ethoxylated with ten molecules of ethylene oxide are heated to 130° – 140°C in vacuo until no further water separates off. 296 parts of the compound of the formula

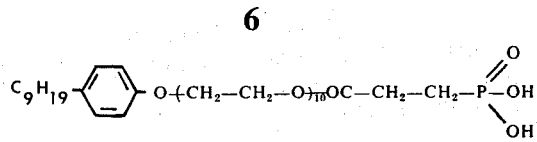

are obtained as a clear, yellowish, highly viscous oil.
Acid number: calculated: 141, found: 135.
Phosphorus content: calculated: 3.89%. found: 4.0%.

The free acid is converted into its mono-potassium salt by addition of 107 parts of a 20% strength aqueous potassium hydroxide solution.

EXAMPLE 7

77 parts of phosphonopropionic acid and 154 parts of a nonylphenol ethoxylated with two molecules of ethylene oxide are heated in vacuo to 130° – 140°C until no further water separates off. 218 parts of the compound of the formula

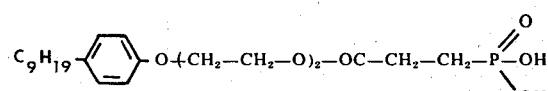

are obtained as a clear, pale brown-coloured, viscous oil.
Acid number: calculated: 252, found: 260.
Phosphorus content: calculated: 6.95%, found: 6.7%.

The free acid is converted into its di-diethanolamine salt by addition of 240 parts of water and 106 parts of diethanolamine.

EXAMPLE 8

46 parts of phosphonopropionic acid and 135 parts of a dodecanol ethoxylated with six molecules of ethylene oxide are heated in vacuo to 130° – 140°C until no further water separates off. 172 parts of the compound of the formula

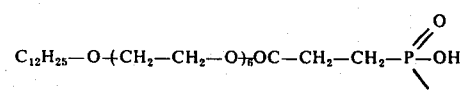

are obtained as a clear, pale brownish-coloured, viscous oil.
Acid number: calculated: 191, found: 184.
Phosphorus content: calculated: 5.28% found: 5.6%.

The free acid is converted into its mono-sodium salt by addition of 40 parts of diethylene glycol, 20 parts of isopropanol and a solution of 13 parts of sodium hydroxide in 40 parts of water.

EXAMPLE 9

Knitted goods of texturised polyethylene glycol terephthalate fibres are introduced, using a liquor ratio of 1:40, into a bath at 60°C which contains, per liter, 0.25 g of the dyestuff

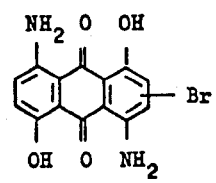

1 g of dinaphthylmethane-disulphonate, 0.2 g of the reaction product of 1 mol of nonylphenol with 10 mols of ethylene oxide, 0.2 g of an ethoxylated fatty acid and 1 g of the phosphonocarboxylic acid ester of the formula

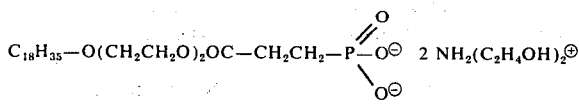

The bath is heated to 125°C over the course of 30 minutes and is kept at this temperature for 60 minutes.

The goods obtained are dyed an even blue, show no creasing whatsoever and have a pleasant soft handle.

Equivalent dyed knitted goods were obtained if instead of the phosphonocarboxylic acid ester salt employed, the same amount of one of the salts described in Examples 1, 2 and 6 was used.

EXAMPLE 10

A fabric of which the warp consists of polyester staple fibre yarn and the weft consists of texturised polyester filament yarn is introduced, on a HT winch, and using a liquor ratio of 1:30, into a bath warmed to 50°C which contains, per liter, 0.75 g of the dyestuff of the formula

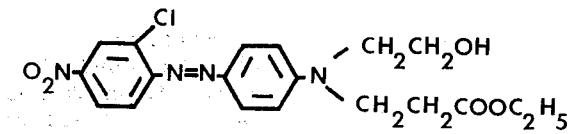

0.2 g of o-hydroxydiphenyl, 0.05 g of dinaphthylmethanedisulphonate and 0.5 g of the phosphonocarboxylic acid ester of the formula

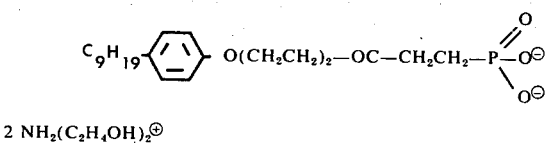

2 $NH_2(C_2H_4OH)_2^\oplus$

The pH value of the liquor is adjusted to 4.5 - 5 by addition of 2 g of disodium hydrogen phosphate and 60% strength acetic acid. The bath is slowly warmed to 125°C and is kept at this temperature for 90 minutes.

The goods obtained are dyed an even scarlet red, have a pleasant soft handle and show no creasing whatsoever in the dried state.

An equivalent dyed fabric was also obtained if instead of the phosphonocarboxylic acid ester salt employed, the same amount of one of the salts described in Examples 1, 2, 3, 4 and 5 was used.

EXAMPLE 11

A knitted fabric of texturised polyester fibres is printed by screen printing with a printing paste consisting of 50 g of the disperse dyestuff of the formula

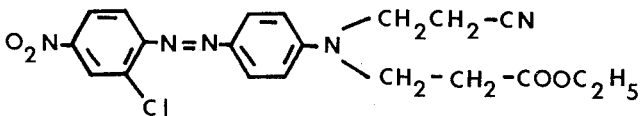

500 g of a thickener consisting of

```
 10 g of prime flour ether
 10 g of alginate (Dialgin HV)
 17 g of starch ether and
463 g of water
 60 g of urea
  5 g of monosodium dihydrogen phosphate
 20 g of the ester salt described in Example 2
355 g of water
1,000 g
```

After drying at 100° to 120°C, the dyestuff is fixed by treating the knitted fabric with hot steam at 165°C for 4 minutes. The fabric is then soaped and rinsed in the usual manner.

A deep scarlet-red print is obtained.

An equivalent print is obtained in equally high dyestuff yield when the dyestuff is fixed by means of dry heat at 180°C and a fabric of cellulose triacetate is used as the textile mixture to be dyed.

I claim:

1. Phosphonocarboxylic acid esters of the formula

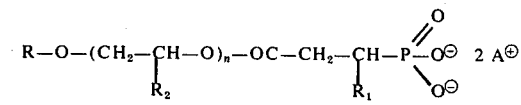

in which
R represents a $C_8$–$C_{22}$-alkyl radical, $C_8$–$C_{22}$-alkenyl radical or $C_8$–$C_{12}$-alkyl-phenyl radical,
$R_1$ represents hydrogen or the

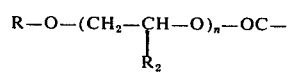

group,
$R_2$ represents hydrogen or the methyl group, $n$ represents a number from 1 to 10 and A represents hydrogen, an alkali metal ion or an ammonium ion.

2. Phosphonocarboxylic acid esters according to claim 1, characterised in that
R represents a $C_{16}$–$C_{22}$-alkyl or $C_{16}$–$C_{22}$-alkenyl radical,
$R_1$ represents hydrogen or the R-O-$(CH_2$-$CH_2$-$O)_N$-OC-group,
$R_2$ represents hydrogen,
$n$ represents a number from 1 to 4 and
A represents an ammonium ion.

3. Phosphonocarboxylic acid ester according to claim 1, of the formula

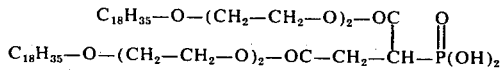

and the corresponding ammonium salts.

4. Phosphonocarboxylic acid esters according to claim 1, of the formula

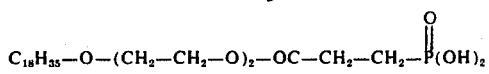
and the corresponding ammonium salts.
5. Phosphonocarboxylic acid esters according to claim 1,
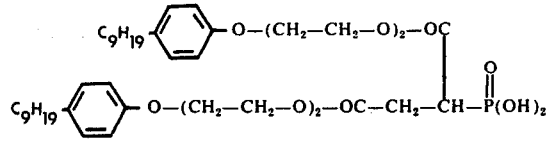
and the corresponding ammonium salts.
6. Phosphonocarboxylic acid ester according to claim 1 of the formula
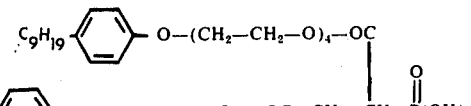
and the corresponding alkali- and ammonium salts.
* * * * *